United States Patent [19]

Schössler et al.

[11] Patent Number: 4,822,681

[45] Date of Patent: Apr. 18, 1989

[54] ACTIVATED POLYMER SOLID BODIES AND PROCESSES FOR THE PRODUCTION THEREOF

[75] Inventors: Werner Schössler, Neu-Buch; Hans-Friedrich Boeden; Martin Holtzhauer, both of Berlin; Fritz Loth, Teltow; Falk Hiepe, Berlin; Dieter Bertram, Leipzig; Frank Mielke, Berlin; Reinhard Müller; Dagmar Konjuchowa, both of Leipzig, all of German Democratic Rep.

[73] Assignee: Veb Leipziger Arzeimittelwerk, Leipzig, German Democratic Rep.

[21] Appl. No.: 9,195

[22] Filed: Jan. 29, 1987

[30] Foreign Application Priority Data

Jan. 29, 1986 [DD] German Democratic Rep. ... 286581
Jan. 29, 1986 [DD] German Democratic Rep. ... 286582

[51] Int. Cl.$^4$ .............................................. B32B 5/12
[52] U.S. Cl. .................................... 428/405; 536/3; 536/31; 536/32; 536/43; 536/51; 536/59; 536/63; 536/84; 536/92; 536/112; 427/399; 525/100; 525/101; 525/102; 525/103; 525/104; 525/105; 528/10; 528/30; 528/36; 528/38; 502/403; 502/407
[58] Field of Search .............. 536/3, 31, 32, 43, 51, 536/59, 63, 84, 92, 112; 428/405; 427/399; 525/100, 101, 102, 103, 104, 105; 528/30, 38, 36, 10; 502/403, 407

[56] References Cited

U.S. PATENT DOCUMENTS 4,627,919 12/1986 Yuki ................................. 502/402
4,654,322 3/1987 Holbein et al. ................ 502/403

*Primary Examiner*—Melvyn I. Marquis
*Attorney, Agent, or Firm*—Michael J. Striker

[57] ABSTRACT

A chemically modified and activated, hydroxyl-group-containing, natural or synthetic, polymeric solid body surface is disclosed, as well as a process for the activation of such solid body surfaces by means of organosilanes and, if necessary, homo- or heterobifunctional reagent. The surfaces are used for the stable, simple and economical binding of proteins, nucleic acids, low-molecular ligands, cells, microorganisms and other biological materials, in biology, biotechnology and medicine.

9 Claims, No Drawings

ACTIVATED POLYMER SOLID BODIES AND PROCESSES FOR THE PRODUCTION THEREOF

BACKGROUND OF THE INVENTION

The invention concerns chemically modified and activated hydroxyl-group-containing natural and synthetic, polymer solid body surfaces, which are employed for the binding of proteins, nucleic acids, low-molecular ligands, cells, microorganisms and other biological materials in fields of biology, biotechnology, as well as medicine, for analytical and preparative purposes, as well as a process for the production thereof.

Carrier-bound biologically active substances have been employed on a broad scale for many years, for the separation and isolation of specific recriprocally-acting partners. See: H. D. Orth, W. Brumer: Angew, Chem. 84 (1972) 319; W. B. Jakob, M. Wilchek (hrsg.): Methods in Enymol. 34 (1974), for binding of enzymes and use as ensyme reactors (K. Mosbach Ohrsg.) Methods in Enzymol. 44 (1976), as well as for qualitative and quantitative display detection of biologically significant compounds in biology, biotechnology, and also increasingly in medicine. In general, the following requirements are placed upon the so-called ideal matrix:

insolubility
macroporosity
mechanical and chemical stability
particular form
hydrophility
low non-specific binding
resistance to microbial and enzymatic influences
presence of functional groups for chemical modifiction and activation Such an ideal matrix, satisfying all of these requirements and thereby universally employable, does not exist. Therefore, in the last several years, a plurality of carrier materials has been described and is commercially available, including natural polymers (polysaccarides), such as dextranes and agarose, also synthetic polymers (such as polyvinyl alcohols, acrylic acid derivatives, vinyl polymers, as well as copolymers of natural and synthetic polymers, such as agarose and polyacrylamide. All of these carriers possess more or less hydroxyl-groups on their surface which are responsible for the hydrophilic characteristics and therewith, low non-specific binding.

Prerequisites for the binding of biologically active substances, such as proteins, lectines, enzymes, nucleic acids, low-molecular ligands, cells and other biological materials, are the introduction, in many cases, the introduction of chemically-active groups, which make possible a chemical binding. The chemical modification designated as "activation" depends principally upon the type of functional groups of the matrix and the ligands, but it is also determined from the chemical stability of the mtrix as well as the stability of the biological characteristics of the ligands. The choice of activation technique is moreover, determined by the technological expense of the activation, and the therewith connected cost of the activation technique, the reactivity of the introduced chemical groups, the possibility for the storage of the activated carrier, the toxicity and biocompatibility of modifcation reagents, as well as the stability of the chemical binding between the solid body surface and the ligand.

Accordingly, it is not surprising with the plurality of limiting parameters and influential factors, that in connection with the numerous carrier materials, a good many activation techniques have been described. Representative of these is the activation technique employing glutaraldehyde or other homo- or heter-bifunctional reagents, the CNBr-activation, the activation with hydrazine, bisepoxiranes, divinyl sulfone, epichlorohydrine, benzoquinone, carbonyl imidazolones, triazine, derivatives, tosylchlorides, as well as the periodate-oxidation and diazotization (See: J. M. Egly, E. Boschetti: Practical guide for use in affinity chromatography and related techniques, IBF-LKB, 1983).

Another technique of substantial employment is the activation by means of bromocyanide introduced by Axen et al. (N. Axen, J. Porath, S. Ernback: Nature 214 (1967) 1302). Whether or not this technique is unequivocally associated with a broad employment of carrier-fixed substances in biotechnology and biology, it is still burdened with the disadvantages of a relatively not-stable chemical binding between solid body surfaces and ligand (particularly at pH values less than 5 and greater than 10), which can lead to a not-inconsiderable setting free of the bound ligands (leakage), and therewith strongly limit the employment mainly for therapeutic in vivo techniques in medicine, the high toxicity of bromocyanide, which economically handicaps the technology of activation, and the danger of formation of cationic groups on the carrier. Disadvantages of the hydrazine activation are the technical problems occurring therewith, as well as the low coupling yields with high-molecular ligands.

Other activation techniques, in contrast, are subject to the disadvantages of the high reagent toxicity (divinyl sulfone, triazine derivatives, epichlorohydrine) and/or high cost of the process (divinyl sulfone, tosylchloride, tresylchloride), unfavorable milieu conditions during the coupling, and therewith the danger of an inactivation of biological materials (Bisepoxirane, Triazine Derivative, Epichlorohydrine), a non-stable binding at high pH values (Divinylsulfone, carbonyldiimidazole, diazonium compounds), long activation and binding periods for ligands (epichlorohydrine, disepoxirane), technological problems, which moreover influence the cost of the technique (triazine derivatives, tosylchloride, carbonyldiimidazol diazotization), low coupling yields (periodate oxidation) as well as relatively strong non-specific binding, attributable in a recriprocally active manner to charge transfer (reciprocal action) (benzoquinone, triazine derivatives, diazonium compounds).

It has been known for a long time (R. A. Messing, H. H. Weetall: U.S. Pat. No. 3,510,538; H. H. Weetall, N.Y., Elmira; U.S. Pat. No. 3,652,761; H. H. Weetall, Methods in Enzymol. 44 (1976), 134) that the OH-groups on $SiO_2$ surfaces, preferably glass, are available as starting points for chemical agents, particularly organosilanes with various functional groups. Moreover, these organosilanes have previously been employed exclusively for inorganic carriers and solid body surfaces.

The aim of the invention is to develop a simple, cost-favorable, non-toxic activation technique for hydroxyl-group-containing, natural and synthetic, polymer solid body surfaces, which lead to stable, activated, solid body surfaces, upon which proteins, nucleic acids, low-molecular ligands, cells, microorganisms and other biological materials can be bound with high stability and yield, as well as biocompatibility.

SUMMARY OF THE INVENTION

It is therefore an object according to the present invention to activate hydroxyl-group-containing natural and synthetic polymer solid body surfaces with compounds which are usually employed for the binding of organic substances onto inorganic substances, whereby highly activated, as well as stable and biocompatible polymer solid bodies should be produced. According to the present invention this object is attained by reacting the hydroxyl-group located on the natural or synthetic solid body surfaces, with an organosilane of the general formula $$(XR'_{n'})_n SiR_{4-n} \qquad (I)$$

whereby X is amino, carbonyl, carboxyl, epoxy, isocyano, diazo, isothiocyano, nitroso, sulfhydryl or halo-carbonyl, and R' is alkyl, alkylphenyl or phenyl, whereas R is an alkoxy, phenoxy or halogen and n' is an integer between 0 and 20 and n is an integer between 1 and 3. Useful organosilanes can be represented by the following formula $$Y_n SiR_{4-n} \qquad (II)$$

in which Y is amino, carbonyl, carboxy, epoxy, or sulfhydryl and R is alkoxy, phenoxy or halogen and n an integer between 1 and 3. In practice, the most broadly and frequently employed organosilanes possess the general composition $$XCH_2CH_2CH_2-Si(OR)_3 \qquad III$$

wherein X is the reactive organic group corresponding to Formula I and R is methyl or ethyl. The reaction is also performed with at least two organosilanes of Formula I, in mixture or successively. The preferred milieu for the organosilane is the liquid or the gaseous phase, whereby the activation can follow in aqueous systems, water/solvent mixtures or organic solvent. If necessary, this can be followed by a further treatment of the modified solid body surfaces with homo- or hetero-bifunctional reagents.

The activated polymer solid body produced by the process according to the present invention, composed of organic OH-group containing macro molecules, possesses on its surface groupings of the general formula $$(-O-)_{4-n} Si(R'_{n'}, X)_n \qquad IV$$

and OH-groups, whereby R' is alkyl, alkylphenyl or phenyl and X is amino, carbonyl, carboxy, epoxy, isocyano, diazo, isothiocyano, nitroso, sulfhydryl or halocarbonyl, and n' is an integer between 0 and 20, with n being an integer between 1 and 3. The ratio of groupings IV to the number of OH-groups lies between 1:9 and 9:1.

Natural and synthetic polymers possess on their surface, as already mentioned, OH-groups, which increase the hydrophilic characteristics of the solid body surfaces and contribute thereby to a reduction in nonspecific, respectively, undesirable reciprocal actions. Whether or not only a fraction of the OH-groups present in the natural and synthetic polymers are supposed to be stearically accessible at the surface of these carriers, it has, surprisingly, been discovered, that organosilanes react with higher reactivity and in higher yield with such solid body surfaces. Whereas the silico-functional group reacts with the accessible hydroxyl-groups of the solid bodies, the organo-functional group is available for the customary chemical reactions, employing amino, carbonyl, carboxyl, isocyano, diazo, isothiocyano, sulfhydryl, nitroso, halocarbonyl groups, so that these compounds function as a bridge between the solid body surface and the organic/biological compound. The so-activated natural or synthetic solid body surfaces can now be reacted directly through the corresponding functional groups or even with the help of homo- or hetero-bifunctional reagents in a manner know per se, with the proteins, lectines, enzymes, nucleic acids, lo-molecular ligands, cells, microorganisms and other biological materials to be bound. This follows according to the present invention, for example, in that the hydroxyl-group-containing solid body surfaces are reacted with γ-aminopropyltriethoxysilane (X=NH$_2$—; R'=(—CH$_2$)$_3$; n'=1; R=—OC$_2$H$_5$; n=1 in Formula I). The amino-groups now located in the solid body surface can be reacted with glutardialdehyde or N-succinimidyl-3-(2-pyridyldithio)propionate (SDPD). The binding of the proteins or other ligands follows in these cases at an aldehyde group across amino-groups (preferably the amino-group of the lysine located in ε-position) or across disulfide-connections.

Analogously, the hydroxyl-group-containing solid body surfaces can be reacted with glycidoxypropyltriethoxysilane. With this variation, the biological materials to be bound react directly with the epoxy-groups of the solid body surface. Herewith it is important that the reaction with the organosilanes, which are non-toxic and are produced to considerable extent on a large scale, be effected by simple contact or immersion, with the activation taking place in swollen or non-swollen state of the solid body, or even in the gaseous phase. It is of greater importance herewith that the reaction with organosilanes can follow in liquid phase with organic solvents, such as acetone, toluene, dioxane, methanol, ethanol, among others, solvent mixtures such as methanol/ethanol, as well as in aqueous milieu or water/solvent mixtures, such as methanol/water or ethanol/water, so that in contrast to many other activation techniques, the technological expenditure is lower. It is particularly advantageous to effect the activation in gaseous phase through employment of aerosols or by means of underpressure. It is, moreover, advantageous that through the choice of different organosilanes and, if necessary, bifunctional coupling reagents, practically all imaginable reaction possibilities can be realized, since by utilization of the basic principle according to the present invention, solid body surfaces are obtained with the most various functional groups (X in Formula I). In addition, as a consequence of the spacer-effect of the organosilane (R'=from 0 to 20) and/or the bifunctional coupling reagents (such as e.g., glutaraldehyde), the bound biological materials retain their biological activity almost without exception. Particularly advantageous is the employment of mixtures of organosilanes of different functional groups, since these can bind biological materials in higher yields through different mechanisms. Thus, for example, mixtures of aminopropyltriethoxysilane and glycidoxypropyltriethoxysilane, as well as aminopropyltriethoxysilane and mercaptopropyltrimethoxysilane proved to be particularly suitable, since these can bind biological materials with very high yield by means of reaction across different functional groups. In these cases, the binding of the ligands is effected across aldehyde and epoxy groups, or across aldehyde or mercapto groupings.

The possibility for reversible coupling of biological materials is available by means of employment of mercaptopropyltrimethoxysilane, since the resulting disulfide-binding can be reversibly split (cleaved) by means of the employment of suitable reducing agent. The reversible ligand-coupling proves to be particularly advantageous in such cases in which the elution of the specifically bound reciprocally acting partners prevents the danger of a denaturization, so that the elution of the protein-ligand-complex is preferred.

The chemical couplings formed by means of reaction of organosilanes with hydroxyl-groups of the natural and synthetic polymers are very stable, so that solid bodies so activated can be stored in dry or wet state over long periods of time, and the bound biologically active ligands remain stable and bound over long time periods even under extreme conditions. The extent of non-specific couplings in natural or synthetic polymer solid body surfaces so activated is extremely low. Organosilanes distinguish by their good biocompatibility.

Coming into consideration as natural or synthetic polymer solid body surfaces are all polymers which are available across a sufficient number of sufficiently stearically accessible hydroxyl-groups at their surface, whereby the composition of the solid body per se is not decisive with respect to the activation technique according to the present invention. Broadly employed are natural polymers based upon cross-polymerized dextranes (Sephadex ®) or polysaccharides based upon agarose (Sepharose ®) or cellulose. Useful synthetic polymers include e.g., cross-polymerized polyvinylalcohols, copolymers of di-, tri- and glycidylmethacrylates with alcohols (Fractogel ®), as well as copolymers derived from N-acryloyl-2-amino-2-hydroxymethyl-1,3-propanediol (Trisacryl ®). Frequently, however, also copolymers of natural and synthetic polymers, such as agarose and polyacrylamide (Ultrogel AcA ®), are employed, which can likewise be activated according to the present invention. Solid bodies of hydroxyethylmethacrylate-ethyleneglycoldimethylacrylate-copolymers, as well as cellulose-containing solid bodies, which are available across a sufficient number of stearically accessible hydroxyl-groups, can likewise be activated with the process according to the present invention.

The solid bodies activated in this manner are expediently provided as shaped bodies, which can possess a spherical, fiber-like or cornered shape, and which can be bound by means of packing, interweaving, or through the use of binding agents, into column packings, surface carriers or other higher-ordered structures. Spherical cellulose-containing solid bodies (e.g., pearl cellulose), are of special importance, since they are mainly employed for chromatographic methods and techniques, and flat carriers ("activated paper") which are broadly employed in analysis and diagnostics. Included, moreover, are thin layers, which are present as films and lacquers on other solid bodies, that do not enter into the reactions according to the present invention, whereby the inert carrier materials for the activation reaction according to the present invention can be homogeneous or non-homogeneous, as well as shaped or non-shaped.

The activated solid body surfaces are employed for the chemical binding or proteins, such as for example antigens, antibodies, enzymes and lectines, nucleic acids, low-molecular ligands, cells, microorganisms and other biological materials. Such ligands bound at solid body surfaces can be employed for separation and isolation of bio-specific reciprocal action partners by means of affinity chromatographic techniques, as enzyme reactors, for qualitative and quantitative determination of biologically significant compounds in the field of biotechnology, biology, and also in medicine.

The novel features which are considered characteristic for the invention are set forth in particular in the appended Claims. The invention itself, however, both as to its construction and its method of operation, together with additional objects and advantages thereof, will be best understood from the following description of specific embodiments.

DESCRIPTION OF THE PREFERRED EMBODIMENTS

Example 1

In each case, 1 g of cross-polymerized Dextrane, (Sephadex ® G 200, Pharmacia, Sweden), Agarose (Sepharose 4 B ®, Pharmacia, Sweden), Trisacryl ® (LKB, Sweden) as well as Fractogel ® (Merck, BRD) are incubated with 5% Aminopropyltriethoxysilane (NB 1114 VEB Chemiewerk Nunchritz, DDR) in ethanol/water (1:1), pH 2.5, for a period of 6 hrs. at 60° C. and then washed twice, each time with 5 ml ethanol/water, as well as five times, each times with 5 ml 0.1 m phosphate-buffer, pH 6.8. Thereafter the degree of activation is determined by evaluation of the amino-groups at the solid body surface according to G. Antoni (Anal. Biochem. 129 [1983]60). The degree of activation can be varied over a broad range by means of the choice of concentration of the organosilane and/or the incubation period. As a rule, one obtains a characteristic degree of activation from 10–30 μMol amino-groups per g of carrier.

Example 2

5 ml Trisacryl ® GF 200 are incubated with 10% aminopropyltriethoxysilane (NB 1114 VEB Chemiewerk Nunchritz, DDR) in ethanol/water (1:1) pH 2.5, for 6 hrs. at 60° C., and then washed twice, each time with 30 ml ethanol/water (1:1) and five times, each time with 20 ml of 0.1 m phosphate-buffer, pH 6.8. The so-activated gel is then reacted with 5% glutaraldehyde for 2 hours at 37° C. in 0.1 m phosphate-buffer pH 6.8, and then washed again, five times, each time with 20 ml phosphate-buffer. The binding of the protein follows by means of simple addition of the protein solution to the gel that has been activated in this manner. The carrier is then reacted with 10 ml human immunoglobulin G in a concentration of 35.5 mg/ml in a 0.1 m phosphate-buffer, pH 6.8, for 2 hours at room temperature. After evacuation in a vacuum of the non-bound portion, a determination of the bound amount of protein on the carrier follows by means of the differential measurement of the albumin concentration of the employed protein solution and the excess portion. In this manner, 49.7 mg IgG.ml Trisacryl are bound.

Example 3

1 ml Trisacryl ® GF 2000 is activated as described in Examples 1 and 2, and reacted with glutaraldehyde in a concentration of 3 percent. The so-activated carrier is then incubated with $^{125}$I-IgG from canines, (directed against alkaline phosphatase) in a concentration of 41.3 mg/ml, and incubated for 2 hours at room temperature.

After evacuation in a vacuum of the excess amount of protein, and subsequent intense washing, each time with 5 ml phosphate-buffer, the bound amount of protein is determined by means of measurement of the radioactivity, the employed protein solution acting as standard. In this test, 32.4 mg $^{125}$I-IgG/ml Trisacryl are bound.

Example 4

1 ml Trisacryl® GF 2000 is brought into contact with a mixture of aminopropyltriethoxysilane as well as blycidoxypropyltriethoxysilane (aided by 6130, VEB Chemiewerk Nunchritz, DDR) and agitated for 2 hours at room temperature. After evacuation in a vacuum of the excess reagent, as well as drying and subsequent washing with 0.1 m phosphate-buffer, pH 6.8, the carrier is reacted with glutaraldehyde and subseuqnetly bound with $^{125}$I-IgG as described in Example 3. There are thus bound 32.7 mg $^{125}$I-IgG/ml Trisacryl.

Example 5

1 ml Sepharose 4 B®, as described in Examples 1 and 2, is activated with silane adhesive and glutaraldehyde, and then reacted with $^{125}$I-IgG, as set forth in Example 3, in a concentration of 41.3 mg/ml in a 0.1 m phosphate-buffer, and incubated for 2 hours at room temperature. The amount of bound protein, which is determined as set forth in Example 3, comes out to 5.6 mg/ml gel.

Example 6

1 ml Sepharose 4 B® as described in Example 4, is activated with two different organosilanes and glutaraldehyde and then reacted with $^{125}$I-IgG. The results indicate a binding of 15.2 mg IgG/ml gel.

Example 7

The gel (Trisacryl) reacted with $^{125}$I-IgG according to Examples 3 and 4 is washed three times, each time with 20 ml of PBS-buffer, pH 7.4, containing 20% Dioxane, and then the bound radioactivity is determined. The amount of bound protein remaining on the Trisacryl is unchanged at 14.3 mg/ml.

Example 8

The Sepharose reacted with $^{125}$I-IgG according to Examples 5 and 6, is intensively washed with a PBS-buffer, containing 20% dioxane, as described in Example 7. The amount of protein indicated by means of determination of radioactivity comes out to 5.6 mg/ml gel (Example 5) or 14.2 mg/ml gel (Example 6).

Example 9

The immunoglobulin G employed in Examples 3–8 is obtained by means of immunization of a canine with the enzyme alkaline phosphatase. It is thereby possible to employ the $^{125}$I-IgG by utilizing the corresponding antibody activity for purification and isolation of the enzyme alkaline phosphatase. Alkaline phosphatase pre-purified by means of n-butanol extraction, is bound to the Sepharose that was reacted with $^{125}$I-IgG according to Example 6, and then eluted with triethylamine, pH 11.4. The so-purified enzyme has a specific activity of 1000 IU/mg, with a yield amounting to about 80%. No accompanying proteins are evident in the polyacrylamide-electrophoresis.

Example 10

Human immunoglobulin G is bound to Trisacryl® GF 2000 as described in Examples 1 and 2, and employed for the isolation of canine anti-human-IgG-antibodies. The IgG-laden carrier is filled to a chromatographic column which is loaded with a specific anti-serum against human-IgG. The elution follows initially with PBS-buffer, and then with a 3 m KSCN-solution. After dialysis of the antibody fractions, a determination of specific antibodies is performed with an enzyme immunoassay as well as the doubled immune diffusion (Ouchterlony technique). The determination of non-specific binding follows by means of employment of corresponding canine-normal serum, as well as testing all antibody-containing fractions by polyacrylamide-disc-electrophoresis.

Example 11

1 g Sepharose 4 B is incubated with 5% mercaptopropyltriemethoxysilane [Serva, BRD] in ethanol/water [1:1], for 4 hours at 60° C., and washed twice, each time with 4 ml ethanol/water, as well as five times, each time with 5 ml of 0.1 m phosphate-buffer pH 6.7. Then the gel is reacted with 10 mg human-IgG which has previously been activated with Npsuccinimidyl 3-(2-pyridyldithio)propionate [SDPD, Pharmacia, Sweden] according to the directions of the manufacturer. The pyridine-2-thione set free upon the reaction can be tracked photometrically at 343 nm. This so-bound IgG can, analogous to Example 10, be employed for the recovery and isolation of the canine-anti-human-IgG-antibodies. After completion of the affinity chromatography, the IgG, bound across disulfide bridges, can be cleaved once again by means of mercaptoethanol or dithiothreitol (50 mM), so that the activated matrix is available for a new binding of a ligand.

Example 12

1 g macroporous, spherical copolymer of 2-hydroxyethylmethacrylate and ethylenedimethacrylate having a particle size of from 15–25 μm and an interior surface of about 70 m$^2$/g carrier, as well as an exclusion limit of 2.10$^6$ Dalton designated Separon® Hema 1000, is incubated with 10% NB 1114 VEB Chemiewerk Nunchritz, DDR in ethanol/water (1:1) pH 2.5, for 6 hrs. at 60° C. and then for another 6 hrs. at 120° C., followed by washing twice, each time with 5 ml ethanol/water, as well as five times, each time with 5 ml. 0.1 m phosphate-buffer, pH 6.8. The degree of activation is then determined by means of the evaluation of the amino-groups on the carrier. Serving for this purpose is the method according to Antoni et al. (Anal. Biochem. 129 [1983,] 60). The degree of activation can be varied over a wide range by means of selection of the concentration of the organosilane and/or the incubation period. As a rule, a degree of activation is obtained of 20 μMol/g Separon.

Example 13

5 g Separon Hema 1000 with a particle size from 15–25 um are incubated for 6 hrs. at 60° C. with 10% aminopropyltriethoxysilane (NB 1114 VEB Chemiewerk Nunchritz, DDR) in ethanol/water (1:1), pH 2.5 and then washed twice, each time with 30 ml ethanol/water (1:1) and five times, each time with 20 ml of 0.1 m phosphate-buffer, pH 6.8. The so-activated gel is then reacted with 5% glutardialdehyde for 2 hrs. at 39° C. in 0.1 m phosphate-buffer, pH 6.8, and then washed again five times, each time with 20 ml. phosphate-buffer. The binding of the protein follows by means of simple addition of the protein solution to the gel that has been activated in this manner. The activated Separon is reacted with 10 ml human immunoglobulin G (IgG) in a concentration of 18.6 mg/ml (0.1 m phosphate-buffer) and incubated for 2 hrs. at 37° C. overnight at 4° C. After evacuation in a vacuum of the non-bound excess, a determination if made of the amount of protein bound on the carrier, by means of differential measurement of the albumin concentration of the employed protein solution and the excess. In this manner, at least )5% of the provided protein is bound in each experiment. In this example, of the 186 mg of IgG provided, 183 mg of protein are bound, so that 36.7 mg IgG/mg Separon are bound.

Example 14

1 ml swollen Separon is activated as described in Examples 12 and 13, and reacted with glutaraldehyde in a concentration of 3%. The so-reacted carried is further reacted with 2 ml human immunoglobulin G in a concentration of 35.5 mg/ml (i.e., 71 mg) in a 0.1 m phosphate-buffer, pH 6.8, 2 hrs. at room temperature. After evacuation in a vacuum of the excess amount of protein, a determination is made of the amount of protein that is bound, as described In Example 13. In this manner, it is determined that 23.6 mg IgG/ml Separon are bound.

Example 15

1 ml swollen Separon is brought into contact with and then agitated for 2 hrs at room temperature with aminopropyltriethoxysilane as well as glycidoxypropyl-triethoxysilane (Haftvermittler 6130, VEB Chemiewerk Nunchritz, DDR). After evacuation in a vacuum of the excess reagent, as well as drying and then intense washing with 0.1 m phosphate-buffer, pH 6.8, the carrier is reacted with glutaraldehyde and then bound with human IgG, as described in Example 14. The result is a binding of 53.8 mg IgG/ml Separon.

Example 16

Human IgG is bound to Separon, as described in Examples 12–15, and employed for the isolation of canine anti-human=IgG-antibodies. The IgG-laden carrier is filled into a chromatographic column which has been loaded with a specific anit-serum against human IgG. The elution follows initially with PBS-buffer, and then with a 3 m solution of KSCN. After dialysis of the antibody fractions, the determination of specific antibodies is performed with an enzyme immunoassay as well as with the doubled radio immune diffusion (Ouchterlony technique). The examination of non-specific coupling follows by means of a corresponding canine-normal serum as well as testing of all antibody-containing fractions by means of polyacrylamide disk-electrophoresis and immunoelectrophoresis.

Example 17

1 g perl cellulose having an exclusion volume of 5,000,000 D and a particle size between 80–200 $\mu$m, as well as a dry substance content of 64 mg/ml is incubated for 6 hrs. at 60° C. with 5% aminopropyltriethoxysilane (NB 1114, VEB Chemiewerk Nunchritz, DDR) in ethanol/water (1:1), pH 2.5 and then washed twice, each time with 5 ml ethanol/water as well as five times, each time with 5 ml 0.1 m phosphate-buffer, pH 6.8. The degree of activation is then found by means of determination of the amino-groups on the solid body surface, according to Antoni (Anal. Biochem. 129 [1983] 60). The degree of activation can be varied over a broad range by means of selection of the concentration of the organosilane and/or of the incubation period. As a rule, characteristic degrees of activation are obtained form 10–15 $\mu$Mol amino-groups per ml of per cellulose.

Example 18

5 ml perl cullulose corresponding to Example 17, are incubated for 6 hrs. at 60° C. with 10% aminopropyl-triethoxysilane in ethanol/water (1:1), pH 2.5 and then washed twice, each time with 30 ml ethanol/water (1:1) and five times, each time with 20 ml of 0.1 phosphite-buffer, pH 6.8. The so-activated gel is then reacted with 5% glutaraldehyde for 2 hrs at 37° C. in 0.1 m phosphate-buffer, pH 6.8, and then washed an additional five times, each time with 20 ml phosphate-buffer. The binding of the protein follows by means of a simple addition of the protein solution to the gel that is activated in this manner. The perl cellulose is reacted with 10 ml human immunoglobulin G in a concentration of 35.5 mg/ml in a 0.1 m phosphate-buffer, pH 6.8, for 2 hrs. at room temperature. After evacuation in a vacuum of the non-bound excess, a determination is made of the amount of protein that is bound, by means of differential measurement of the albumin concentration of the employed protein solution and of the excess. In this manner, 12 mg of IgG/ml perl cellulose are bound.

Example 19

1 ml perl cellulose, as described in Example 18, is activated and then reacted with glutaraldehyde in a concentration of 3%. Then, the so-activated carrier is reacted with $^{125}$I-IgG (from canines, directed against the enzyme alkaline phosphatase) in a concentration of 41.3 mg/ml, and incubated for 1 hr. at room temperature. After evacuation in a vacuum of the excess amount of protein and subsequent intense washing with always 5 ml phosphate-buffer, the bound amount of protein is determined by means of measurement of the radioactivity, the employed protein solution acting as standard. In this test, 11.4 mg of $^{125}$I-IgG/ml perl cellulose are bound.

Example 20

5 ml perl cellulose, as described in Example 17, are incubated for 6 hrs. at 60° C. with 5% glycidoxypropyl-triethoxysilane (NB 115, VEB Chemiewerk Nunchritz, DDR) in ethanol/water (1:1), pH 2.5, and then heated a further 6 hrs. to 120° C. After intense washing, each time with 20 ml. ehtanol/water and 0.1 phosphate-buffer, analogous to Example 18, the so-called activated perl cellulose is reacted for 3 hrs. at room temperature with 10 ml human immunoglobulin G in a concentration of 35.5 mg/ml in a 0.1 phosphate-buffer, pH 6.8. The bound amount of protein, which is determined as described in Example 18, comes out to 7.2 mg of IgG/ml perl cellulose.

Example 21

5 ml perl cellulose, corresponding to Example 17, are incubated for 4 hrs. at 60° C. with 5% mercaptopropyl-trimethoxysilane (Serva, BRD) in ethanol/water (1:1) and then washed, each time with 5 ml ethanol/water as well as five times, each time with 5 ml 0.1 m phosphate-buffer, pH 6.8. The cellulose is then reacted with 10 mg human IgG, which has previously been activated with N-succinimidyl-3-(2-pyridyldithio)propionate (SDPD, Phmarmacia, Sweden) according to the directions of the manufacturer. The pyridine-2-thione set free upon the reaction is seen photometrically at 343 nm. The so-bound IgG can be employed for the recovery and isolation of canine-anti-human=IgG-antibodies. After running the affinity chromatography, the IgG bound across disulfide bridges, can be cleaved once again by means of mercaptoethanol or dithiothreitol (50 mM), so that the activated matrix is available again for the binding of a ligand.

Example 22

5 ml. perl cellulose, corresponding to Example 17, are brought into contact with a mixture of aminopropyltriethanoxysilane and glycidoxypropyltriethoxysilane (Haftvermittler 6130, VEB Chemiewerk Nunchritz, DDR) and agitated for 2 hrs. at room temperature. After evacuation in a vacuum of the excess reagent, as well as drying in a vacuum and subsequent intense washing with 0.1 m phosphate-buffer, pH 6.8, the carrier is reacted with 3% glutaraldehyde and then bound, as described in Example 19, with $^{125}$I-IgG. There are bound 26.4 mg $^{125}$-I-IgG/ml perl cellulose.

Example 23

The perl cellulose reacted with $^{125}$I-IgG according to Example 22, is washed three times, each time with 20 ml PBS-buffer, pH 7.4, containing Dioxane and then a determination is made of the bound radioactivity. The amount of proteins remaining on the perl cellulose are unchanged at 11.4 mg/ml (Example 19) and 26.6 mg/ml (Example 22).

Example 24

The immunoglobulin G employed in Examples 19, 22 and 23, is obtained by means of immunization of a dog with the enzyme alkaline phosphatase. It is possible to employ the $^{125}$I-IgG with utilization of the corresponding antibody activities for the purification and isolation of the enzyme alkaline phosphatase. Alkaline phosphatase, pre-purified by means of n-butanol extraction is bound to the perl cellulose that has been reacted according to Example 19 with $^{125}$-I-IgG, and then eluted with triethylamine, pH 11.4. The so-purified enzyme has a specific activity of 1000 IU/mg, whereby the yield amounts to about 80%. No accompanying proteins are evident in the polyacrylamide-electrophoresis.

Example 25

Human immunoglobulin G, as set forth in Example 18, is bound to perl cellulose and employed for the isolation of canine-anti-human-IgG-antibodies. The carrier, loaded with IgG, is filled into a chromatographic column which in turn, is loaded with a specific antiserum against human IgG. The elution follows initially with PBS-buffer and subsequently with a 3 m solution of KSCN. After dialysis of the antibody fractions, a determination of specific antibodies is effected with an enzyme immunoassay, as well as the doubled radio immune diffusion (Ouchter-Iony technique). The testing for non-specific coupling follow swith a corresponding canine-normal serum, as well as testing of all antibody-containing fractions by polyacrylamide-disc-electrophoresis.

Example 26

Flat-shaped cellulose carriers (Whatman-Papier 560 and FN 4-Papier) are actived as described in Examples 19 and 20 with 3% aminopropyltriethoxysilane or glycidoxypropylsilane and then reacted with 131I-human serum albumin ($^{131}$-I-HSA) in 0.1 phosphate-buffer, pH 6.8, in a concentration of 10 ug/ml and 100 ug/ml. After intense washing, the bound amount of protein is determined by means of a measurement of the radioactivity using a standard. The results obtained are summarized in the following table:

TABLE 1

| Employed Protein Conc. | Bound $^{131}$I-HSA | | | |
|---|---|---|---|---|
| | Aminopropyltriethoxysilane | | Glycidoxypropyltriethoxysilane | |
| | 10 μg/ml | 100 μg/ml | 10 μg/ml | 100 μg/ml |
| FN 4 | 192 ng/cm² | 1036 ng/cm² | 75 ng/cm² | 343 ng/cm² |
| Whatman 580 | 61 ng/cm² | 486 ng/cm² | 15 ng/cm² | 76 ng/cm² |

Example 27

The paper carrier loaded according to Example 26, with $^{131}$I-HSA is employed as follows in enzymeimmunoassay. Defined surfaces of this carrier, after preliminary blocking of possibly still free reactive groups with ethanolamin, are reacted with a canine-anti-human-albumin-antiserum in suitable dilution, and incubated overnight at room temperature. After washing three times for the removal of the non-bound antibodies, the paper carrier is incubated with a goat-anti-canine-IgG-conjugate (enzyme: alkaline phosphatase) for 4 hrs. at 37° C., and then washed again three times. The enzyme activity is determined by hydrolysis from 4-nitrophenylphosphate in 0.5 ml diethanolamine-buffer, pH 9.8 and photometric measurement of the enzyme product at 405 nm.

Example 28

Flat-shaped cellulose carrier (Whatman 560, Filtrak 1389, Filtrak 309, FN 3), as described in Example 22, is activated with a mixture of aminipropyltriethoxysilane and glycidoxypropyltriethoxysilane and then incubated with $^{125}$I-IgG (directed against the enzyme alkaline phosphatase) in two concentrations in 0.1 phosphate-buffer, pH 6.8. After washing three times with a PBS-buffer, the amount of bound protein is determined by measurement of the radioactivity. Then, the flat-shaped cellulose carrier is washed again ten times with PBS buffer, and the amount of bound protein is again determined by measurement of the radioactivity, using a standard. Finally, the cellulose carrier is washed numerous times over a period of 4 weeks with HCl-glycine-buffer, pH 2.2, 3 m KSCN, carbonate-bicarbonate-buffer, pH 10, and PBS-buffer, containing 20% Dioane, and employed anew for the determination of the bound amount of protein.

The results are set forth in the following table:

TABLE 2

| | Bound $^{125}$I-IgG | | | |
|---|---|---|---|---|
| | Whatman 560 | Filtrak 1389 | Filtrak 380 | FN 3 |
| Bound protein after 3 washings | | | | |
| 10 μg/ml | 2092 ng/cm² | 2143 ng/cm² | 2015 ng/cm² | 2372 ng/cm² |

TABLE 2-continued

| | Bound $^{125}$I-IgG | | | |
|---|---|---|---|---|
| | Whatman 560 | Filtrak 1389 | Filtrak 380 | FN 3 |
| 50 μg/ml | 5536 ng/cm$^2$ | 6122 ng/cm$^2$ | 5867 ng/cm$^2$ | 5867 ng/cm$^2$ |
| Bound protein after additional washings | | | | |
| 10 μg/ml | 1888 ng/cm$^2$ | 1939 ng/cm$^2$ | 1786 ng/cm$^2$ | 2092 ng/cm$^2$ |
| 50 μg/ml | 5000 ng/cm$^2$ | 5612 ng/cm$^2$ | 5281 ng/cm$^2$ | 5459 ng/cm$^2$ |
| Bound protein after 4 weeks | | | | |
| 10 μg/ml | 1913 ng/cm$^2$ | 1913 ng/cm$^2$ | 1786 ng/cm$^2$ | 1964 ng/cm$^2$ |
| 50 μg/ml | 5102 ng/cm$^2$ | 5612 ng/cm$^2$ | 5306 ng/cm$^2$ | 5281 ng/cm$^2$ |

Example 29

A flat carrier with paper-like matrix according to the present invention is reacted with human immunoglublin G that has been marked radioactively with $^{125}$I, in various concentrations and buffer systems, and incubated for 16 hrs. at 37° C. After washing three times with PBS-buffer, pH 7.4, containing 0.05% Tween 20, the possibly still excess reactive groups are blocked with 1 m ethanolamine solution. After further washing with the above PBS-buffers, the bound amount of protein is determined by measurement of radioactivity. For determination of possible desorbtion, the samples are subsequently washed again, seven times with PBS-buffer. The so-laden flat carriers are then reacted with a conjugate composed of a canine-anti-human-IgG and the enzyme alkaline phosphatase for determination of the immunoactivity, and incubated overnight at room temperature. After further washing, the enzyme activity of the alkaline phosphatase is determined by means of hydrolysis from human IgG and the enzyme 4-nitrophenylphosphate in 0.5 ml diethanolamine buffer, pH 9.8 and photometric measurement of the enzym product at 405 nm after stopping with 1 n NaOH of 1 n EDTA. After performance of the enzyme immunoassay, the flat carriers are washed twice, each time with 0.5 ml of PBS-buffer, and reacted in series tests with one of the following dissociation reagents for 1 hr. at 4° C.:

(1) PBS-buffer, 2 m in NaCl, containing 5% Dioxane;
(2) 1 m KSCN;
(3) 3 m KSCN;
(4) 4.5 m. MgCl$_2$;
(5) 1 m NaI;
(6) HCl-glycine-buffer, pH 2.8.

By means of all these agents, the bound antigen-antibody-complex is cleaved, so that the flat carrier, loaded with human IgG, can be employed again in enzyume immunoassay.

Example 30

Flat-shaped bodies according to the present invention (F=56 mm$^2$) are activated, as described in Example 22 and loaded with human factor VIII. These carriers are arranged in polystyrene-microtitration-plates or polystyrene tubes. An enzyme immunoassay is then performed in the described manner for determination of F VIII-antigen (W. Schobler, M. Stepanauskas, Chr. Dittrich, H. Heine: Acta. biol. med, germ. 41 (1982) 263; W. Schobler, M. Stepanauskas, Chri, Dittrich: Acta biol. med. germ. 41 (1982) 965. The shaped bodies are reacted with an incubation mixture composed of the plasma to be determined and a canine-anti-human-Factor VIII-antibody provided in excess, and incubated for 6 hrs. at 37° C. After washing with PBS-buffer, pH 7.4, containing 0.05% Tween 20, 200 ul of a conjugate composed of a sheep-anti-canine-IgG and the enzyme alkaline phosphatase, are added, upon which after several hours incubation and subsequent washing, the enzyme activity is determined as described in Example 29. The cleaving of the bound antibody follows with one of the dissociation reagents set forth in Example 29, so that the carrier, laden with Factor VIII, can be employed anew in immunoassay.

Example 31

A flat carrier according to the present invention with paper-like matrix, is loaded with human Factor VIII as described in Example 30. This carrier serves then as a module for screening tests with (monoclonal) antibodies. After performance of the washing operation, which is particularly simple with a flat carrier, the substances to be tested and determined are applied with a suitable application stamp in the form of dots. Suitable dilutions of a canine-anti-human Factor VIII-anti-serum, respectively a canine serum as negative control, serve as antibody source. After an incubation of 4–6 hrs. at 37° C., the flat carriers are washed again and incubated with a sheep-anti-canine IgG, coupled with the enzyme peroxidase, 4 hrs. at 37° C. or overnight at room temperature. Then follows several washings, and the enzyme activity is determined with a suitable system, thus e.g., 4 mM 0-phenylenediamine and 1.5 mM H$_2$O$_2$ by means of visual evaluation of the produced coloration. A positive coloration clearly indicates an antibody.

Example 32

$^{32}$P-marked phosphoprotein, which is contained in membrane vesicles of heart muscle are separated in the phosphate-buffered sodium dodecylsulfate-polyacrylamide-gel-electrophoresis system according to Weber et al. (K. Weber, J. Pringle, M. Osborn, Meth. Enzymol. 26, [1972] 3). After termination of the electrophoresis, the separated proteins on the paper activated according to the present invention, are subjected to immunoblotting in a triethanolamine and butyric acid containing a transfer system as per Kyhse-Anderson (J. Biochem. Biphys. Meth. 10 [1984] 203). After the blotting, they are bathed in phosphate-buffered physiological Koch's salt solution containing 0.1% gelatin and 0.05% Tween, subsequently incubated with a first canine-anti-serum, and followed by incubation with an anti-canine-immunoglobulin horse radish peroxidase conjugate. Finally, there follows the indicator reaction. In place of the peroxidase-conjugate, an alkaline phosphatase-conjugate can be employed with similar results.

Example 33

The protein intracellular membranes of various muscle cell types are separated in a dodecylsulfate-polyacrylamide-electrophoresis system as per Laemmll (U. K. Laemmll, Nature 227 [1970] 680). After the electrophoresis, the gel is bathed for 20–60 minutes in a buffer solution composed of 25 mM triethanolamine-hydrochloride, pH 8.4, 0.1% sodium dodecylsulfate. The immunoblotting is effected directly thereafter, as set forth in Example 32.

It will be understood that each of the elements described above, or two or more together, may also find a useful application in other types of surface modifications and chemical quantitative and qualitative analyses different from the types described above.

While the invention has been illustrated and described as embodied in activated polymer solid bodies and processes for the production thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Process for the activation of hydroxyl group-containing polymeric solid body carrier material surfaces, comprising reacting said hydroxyl groups to form chemical bonding with an organo-silane of the formula (I)

$$(XR'_{n'})_n SiR_{4-n} \qquad (I)$$

in which X carbonyl, carboxy, epoxy, isocyano, isothiocyano, nitroso, sulfhydryl or halocarbonyl, R' is alkyl, alkylphenyl or phenyl, R is alkoxy, phenoxy or halogen, n' is an integer from 0 to 20 and n is an integer from 1 to 3, or with two or more organo-silanes of formula (I), said two or more organo-silanes being provided together in mixture, or successively, said organo-silane being provided in a fluid phase.

2. The process according to claim 1, wherein said reacting hydroxyl groups with organo-silane is effected in solution selected from the group consisting of organic solvent, organic solvent mixtures, aqueous solution and aqueous/organic solvent mixtures.

3. The process according to claim 1, wherein said reacting hydroxyl groups to form chemical bonding with organo-silane is effected in gaseous phase by means of aerosol spraying said organo-silane onto said carrier matrix surfaces.

4. The process according to claim 1, wherein said reacting hydroxyl groups with organo-silane is effected at a pressure below atmospheric pressure.

5. The process according to claim 1, wherein said polymeric solid body comprises a shaped body.

6. The process according to claim 5, wherein said shaped body comprises a spherical, fiber-like or cornered shape.

7. The process according to claim 5, wherein said shaped body comprises a ball shape.

8. The process according to claim 5, wherein a plurality of said shaped body are grouped together by means of packing, interweaving or binding agent into column packing or laminar material.

9. The process according to claim 5, wherein said shaped body is provided in the form of a thin layer as a film or lacquer on other carriers.

* * * * *